US012475987B2

(12) United States Patent
Duclos et al.

(10) Patent No.: US 12,475,987 B2
(45) Date of Patent: Nov. 18, 2025

(54) ROBOTICALLY-ASSISTED DRUG DELIVERY

(71) Applicant: Medtronic Navigation, Inc., Louisville, CO (US)

(72) Inventors: Brian A. Duclos, Blaine, MN (US); Vinod Sharma, Maple Grove, MN (US)

(73) Assignee: Medtronic Navigation, Inc., Louisville, CO (US)

( * ) Notice: Subject to any disclaimer, the term of this patent is extended or adjusted under 35 U.S.C. 154(b) by 294 days.

(21) Appl. No.: 17/948,469

(22) Filed: Sep. 20, 2022

(65) Prior Publication Data

US 2024/0096472 A1 Mar. 21, 2024

(51) Int. Cl.
*G16H 20/17* (2018.01)

(52) U.S. Cl.
CPC .................................. *G16H 20/17* (2018.01)

(58) Field of Classification Search
CPC ...................................................... G16H 20/17
See application file for complete search history.

(56) References Cited

U.S. PATENT DOCUMENTS 3,739,777 A * 6/1973 Gregg ................ A61M 5/1689 340/610
5,178,603 A * 1/1993 Prince ................... A61M 1/308 604/6.11
5,919,135 A * 7/1999 Lemelson ............. A61B 5/704 600/407
6,569,148 B2 * 5/2003 Bagaoisan ........ A61M 25/0075 604/509
10,391,238 B2 * 8/2019 Guo ...................... A61M 5/172
2006/0224140 A1 * 10/2006 Junker .............. A61M 5/14276 604/502
2008/0167674 A1 7/2008 Bodduluri et al.
2011/0009812 A1 * 1/2011 Brown .................. G16H 40/63 604/36
2012/0053562 A1 * 3/2012 Haase .............. A61M 5/14216 604/93.01
2012/0065618 A1 * 3/2012 Stearns .............. A61M 5/1785 604/506

(Continued)

FOREIGN PATENT DOCUMENTS

CN 103827873 A * 5/2014 ........ A61M 5/14546
CN 106730149 A * 5/2017 ........... A61M 5/158

(Continued)

OTHER PUBLICATIONS

International Search Report and Written Opinion for International (PCT) Patent Application No. PCT/IB2023/059129, dated Jan. 4, 2024, 13 pages.

*Primary Examiner* — Kenneth Bartley
(74) *Attorney, Agent, or Firm* — Sheridan Ross P.C.

(57) ABSTRACT

A system includes a processor and a memory storing instructions thereon. The instructions, when executed by the processor, cause the processor to: infuse a substance into a target object, via an infusion device, according to a first flow rate; set a second flow rate associated with infusing the substance into the target object, based on a withdrawal rate of the infusion device from the target object; and infuse the substance into the target object based on the second flow rate.

30 Claims, 4 Drawing Sheets

(56) References Cited

U.S. PATENT DOCUMENTS

| | | | | |
|---|---|---|---|---|
| 2013/0150821 | A1* | 6/2013 | Bollish | A61M 5/16895 422/44 |
| 2013/0211374 | A1* | 8/2013 | Hetherington | A61B 17/8822 604/506 |
| 2014/0012226 | A1* | 1/2014 | Hochman | A61M 5/168 604/67 |
| 2014/0088553 | A1* | 3/2014 | Hetherington | A61M 5/31511 604/211 |
| 2014/0221910 | A1* | 8/2014 | Mastalli | A61M 1/28 705/2 |
| 2014/0358114 | A1 | 12/2014 | Rosenbluth et al. | |
| 2015/0119663 | A1* | 4/2015 | Lim | A61B 5/1427 600/309 |
| 2015/0224260 | A1* | 8/2015 | Stearns | A61M 5/1785 604/506 |
| 2016/0259913 | A1* | 9/2016 | Yu | A61M 5/31511 |
| 2018/0099085 | A1* | 4/2018 | Guo | A61M 5/142 |
| 2023/0193183 | A1* | 6/2023 | Tilley | C12M 21/08 425/375 |
| 2024/0041480 | A1* | 2/2024 | Bartholomew | A61M 5/1408 |
| 2024/0042124 | A1* | 2/2024 | Bartholomew | A61M 25/0097 |
| 2024/0042142 | A1* | 2/2024 | Bartholomew | A61M 25/0097 |
| 2024/0200011 | A1* | 6/2024 | Tilley | C12M 33/00 |

FOREIGN PATENT DOCUMENTS

| | | | | |
|---|---|---|---|---|
| CN | 112561900 | | 3/2021 | |
| CN | 112561900 | A * | 3/2021 | |
| WO | WO-2011005679 | A1 * | 1/2011 | A61B 10/0045 |
| WO | WO-2024030406 | A1 * | 2/2024 | A61M 25/0097 |

* cited by examiner

ROBOTICALLY-ASSISTED DRUG DELIVERY

FIELD OF INVENTION

The present disclosure is generally directed to drug delivery, and relates more particularly to robotically-assisted drug delivery.

BACKGROUND

Robots may assist a surgeon or other medical provider in carrying out a medical procedure (e.g., a surgical procedure, a treatment, etc.), or may complete one or more medical procedures autonomously. Imaging may be used by a medical provider for diagnostic and/or therapeutic purposes.

BRIEF SUMMARY

Example aspects of the present disclosure include:

A system including: a processor; and a memory storing instructions thereon that, when executed by the processor, cause the processor to: infuse a substance into a target object, via an infusion device, according to a first flow rate; set a second flow rate associated with infusing the substance into the target object, based on a withdrawal rate of the infusion device from the target object; and infuse the substance into the target object based on the second flow rate.

A system including: an infusion device; a processor; and a memory storing data thereon that, when processed by the processor, cause the processor to: infuse a substance into a target object, via the infusion device, according to a first flow rate; set a second flow rate associated with infusing the substance into the target object, based on a withdrawal rate of the infusion device from the target object; and infuse the substance into the target object based on the second flow rate.

A method including: infusing a substance into a target object, via an infusion device, according to a first flow rate; setting a second flow rate associated with infusing the substance into the target object, in response to determining a withdrawal rate associated with withdrawing the infusion device from the target object; and infusing the substance into the target object based on the second flow rate.

A system, including: an infusion device; a robot device; infusion management circuitry that controls infusion of a substance by: infusing the substance into a target object, via the robot device and the infusion device, according to a first flow rate; setting a second flow rate associated with infusing the substance into the target object, based on a withdrawal rate of the infusion device from the target object; and infusing the substance into the target object based on the second flow rate.

A non-transitory computer readable medium including instructions, which when executed by a processor: infuse a substance into a target object, via an infusion device, according to a first flow rate; set a second flow rate associated with infusing the substance into the target object, based on a withdrawal rate of the infusion device from the target object; and infuse the substance into the target object based on the second flow rate.

Any aspect in combination with any one or more other aspects.

Any one or more of the features disclosed herein.

Any one or more of the features as substantially disclosed herein.

Any one or more of the features as substantially disclosed herein in combination with any one or more other features as substantially disclosed herein.

Any one of the aspects/features/implementations in combination with any one or more other aspects/features/implementations.

Use of any one or more of the aspects or features as disclosed herein.

It is to be appreciated that any feature described herein can be claimed in combination with any other feature(s) as described herein, regardless of whether the features come from the same described implementation.

The details of one or more aspects of the disclosure are set forth in the accompanying drawings and the description below. Other features, objects, and advantages of the techniques described in this disclosure will be apparent from the description and drawings, and from the claims.

The preceding is a simplified summary of the disclosure to provide an understanding of some aspects of the disclosure. This summary is neither an extensive nor exhaustive overview of the disclosure and its various aspects, implementations, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, implementations, and configurations of the disclosure are possible utilizing, alone or in combination, one or more of the features set forth above or described in detail below.

Numerous additional features and advantages of the present disclosure will become apparent to those skilled in the art upon consideration of the implementation descriptions provided hereinbelow.

BRIEF DESCRIPTION OF THE SEVERAL VIEWS OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure can be made and used and are not to be construed as limiting the disclosure to only the illustrated and described examples. Further features and advantages will become apparent from the following, more detailed, description of the various aspects, implementations, and configurations of the disclosure, as illustrated by the drawings referenced below.

DETAILED DESCRIPTION

Figure 1A:
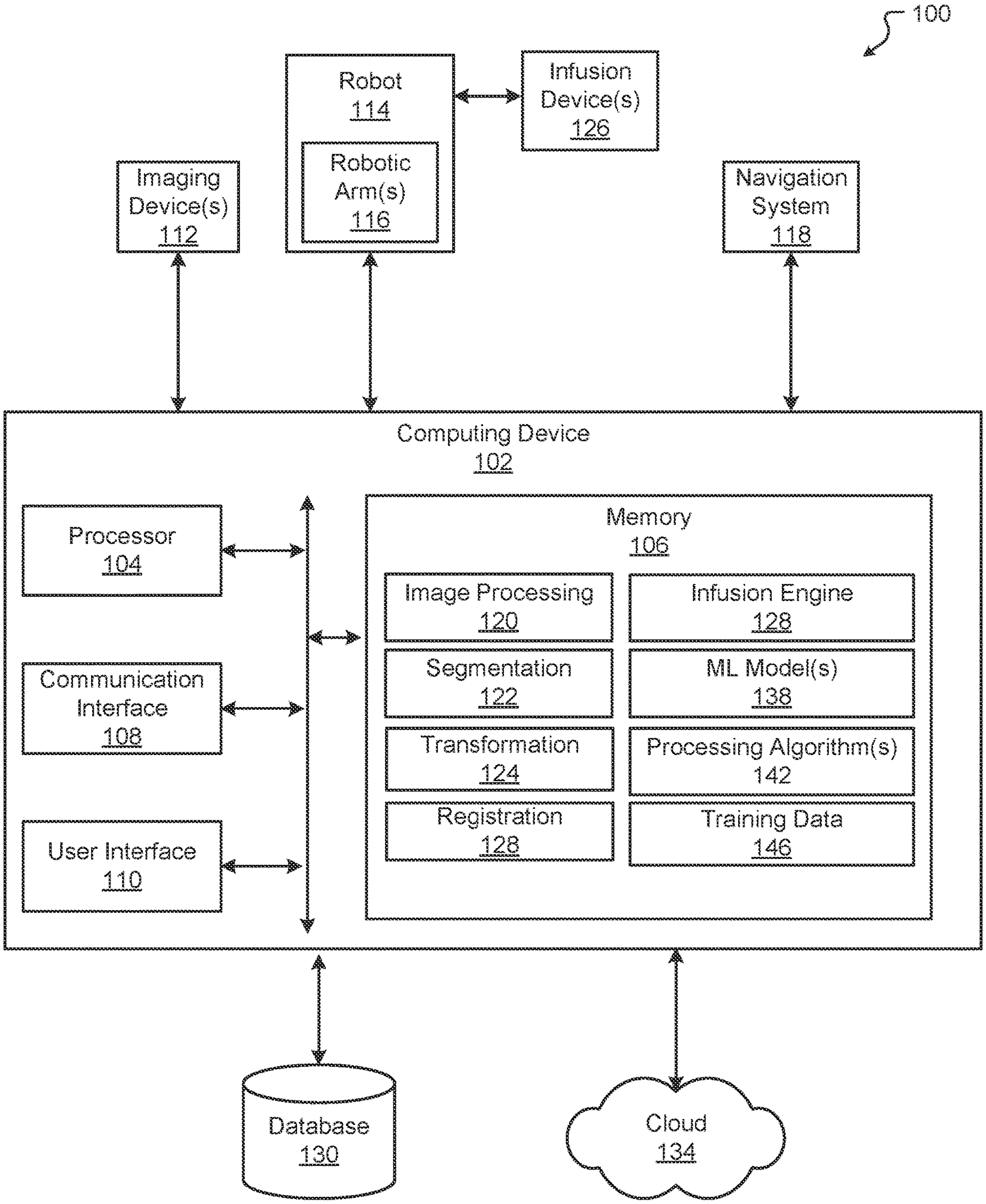
FIGS. 1A and 1B illustrate examples of a system that support aspects of the present disclosure.

It should be understood that various aspects disclosed herein may be combined in different combinations than the combinations specifically presented in the description and accompanying drawings. It should also be understood that, depending on the example or implementation, certain acts or events of any of the processes or methods described herein may be performed in a different sequence, and/or may be added, merged, or left out altogether (e.g., all described acts or events may not be necessary to carry out the disclosed techniques according to different implementations of the present disclosure). In addition, while certain aspects of this disclosure are described as being performed by a single module or unit for purposes of clarity, it should be understood that the techniques of this disclosure may be performed by a combination of units or modules associated with, for example, a computing device and/or a medical device.

In one or more examples, the described methods, processes, and techniques may be implemented in hardware, software, firmware, or any combination thereof. If implemented in software, the functions may be stored as one or more instructions or code on a computer-readable medium and executed by a hardware-based processing unit. Alternatively or additionally, functions may be implemented using machine learning models, neural networks, artificial neural networks, or combinations thereof (alone or in combination with instructions). Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors (e.g., Intel Core i3, i5, i7, or i9 processors; Intel Celeron processors; Intel Xeon processors; Intel Pentium processors; AMD Ryzen processors; AMD Athlon processors; AMD Phenom processors; Apple A10 or 10X Fusion processors; Apple A11, A12, A12X, A12Z, or A13 Bionic processors; or any other general purpose microprocessors), graphics processing units (e.g., Nvidia GeForce RTX 2000-series processors, Nvidia GeForce RTX 3000-series processors, AMD Radeon RX 5000-series processors, AMD Radeon RX 6000-series processors, or any other graphics processing units), application specific integrated circuits (ASICs), field programmable logic arrays (FPGAs), or other equivalent integrated or discrete logic circuitry. Accordingly, the term “processor” as used herein may refer to any of the foregoing structure or any other physical structure suitable for implementation of the described techniques. Also, the techniques could be fully implemented in one or more circuits or logic elements.

Before any implementations of the disclosure are explained in detail, it is to be understood that the disclosure is not limited in its application to the details of construction and the arrangement of components set forth in the following description or illustrated in the drawings. The disclosure is capable of other implementations and of being practiced or of being carried out in various ways. Also, it is to be understood that the phraseology and terminology used herein is for the purpose of description and should not be regarded as limiting. The use of “including,” “comprising,” or “having” and variations thereof herein is meant to encompass the items listed thereafter and equivalents thereof as well as additional items. Further, the present disclosure may use examples to illustrate one or more aspects thereof. Unless explicitly stated otherwise, the use or listing of one or more examples (which may be denoted by “for example,” “by way of example,” “e.g.,” “such as,” or similar language) is not intended to and does not limit the scope of the present disclosure.

The terms proximal and distal are used in this disclosure with their conventional medical meanings, proximal being closer to the operator or user of the system, and further from the region of surgical interest in or on the patient, and distal being closer to the region of surgical interest in or on the patient, and further from the operator or user of the system.

Location of drug delivery and coverage of a target object is of paramount importance in targeted drug delivery of therapeutics. For example, location and drug delivery and coverage is critical in the targeted drug delivery of small molecules, proteins, gene therapies, therapeutic antibodies, nucleic acid therapeutics and cell-based therapies in the brain, as well as for oncological needs such as glioblastoma. Some techniques utilize magnetic resonance imaging (MM) and manual guidance of therapy deployment by specialized surgeons using MM contrast agents (e.g., gadolinium-based contrast agents) in conjunction with the therapeutic.

Aspects of the present disclosure include a robotically-assisted deployment supportive of increasing patient access to targeted drug delivery outside of highly specialized academic institutions. In some implementations, patients are imaged with MM-Computed Tomography (CT) prior to surgery to visualize a region of interest (ROI). Using the visualization, a robotic system may identify the navigational coordinates of a targeted structure or mass, along with the size and shape thereof. The robotic system may provide automated, robotic deployment of an infusion rate, cannula movement, and placement (e.g., calculate and implement optimal infusion rate, cannula movement, and placement) for a patient to afford maximal structural coverage. The robotic system may support robotically-assisted drug delivery, and in some examples, robotically-assisted brain drug delivery algorithms for implementing the same. In some embodiments, aspects of robotically-assisted drug delivery described herein support drug delivery (e.g., of small molecules and proteins, therapeutic antibodies, etc.) in association with any combination of therapeutic modalities.

Aspects of the robotic deployment described herein may provide increased benefits when targeting multiple structures with two or more cannulas. For example, drug delivery using the cannulas may respectively involve different placements and infusion rates for effective coverage, which may be highly challenging in cases of manual administration. In an example, according to some other techniques, a physician may initiate delivery of a drug (e.g., via a cannula) and attempt to manually withdraw the cannula while the drug is being dispensed. Such manual approaches, however, are dependent on the respective experience and ability of the physician. Aspects of the systems described herein may provide calculated infusion rates that support increased coverage in association with drug delivery.

According to example aspects of the present disclosure, a robot device may provide improved precision with respect to controlling infusion rate and withdrawal of an infusion device. In some aspects, the robot device may obtain coordinate information from a neural navigation system in association with guiding and withdrawing the infusion device. For example, using the coordinate information, the robot device may deliver a medical substance to a target object (e.g., target tissue) with improved accuracy, reducing potential bleed through of the medical substance to other tissue. Accordingly, for example, a robot device described herein may be capable of providing effective drug delivery tailored to a patient, with reduced reliance on a medical specialist. The terms ‘robot device,’ ‘robotic device,’ and ‘robot’ may be used interchangeably herein.

FIG. 1A illustrates an example of a system 100 that supports aspects of the present disclosure.

The system 100 includes a computing device 102, one or more imaging devices 112, a robot 114, a navigation system

118, an infusion device 126, a database 130, and/or a cloud network 134 (or other network). Systems according to other implementations of the present disclosure may include more or fewer components than the system 100. For example, the system 100 may omit and/or include additional instances of one or more components of the computing device 102, the imaging device(s) 112, the robot 114, navigation system 118, the infusion device 126, the database 130, and/or the cloud network 134. In an example, the system 100 may omit any instance of the computing device 102, the imaging device(s) 112, the robot 114, navigation system 118, the database 130, and/or the cloud network 134. The system 100 may support the implementation of one or more other aspects of one or more of the methods disclosed herein.

The computing device 102 includes a processor 104, a memory 106, a communication interface 108, and a user interface 110. Computing devices according to other implementations of the present disclosure may include more or fewer components than the computing device 102. The computing device 102 may be, for example, a control device including electronic circuitry associated with controlling the robot 114, the robotic arm(s) 116, and/or the infusion device 126.

The processor 104 of the computing device 102 may be any processor described herein or any similar processor. The processor 104 may be configured to execute instructions stored in the memory 106, which instructions may cause the processor 104 to carry out one or more computing operations utilizing or based on data received from the imaging devices 112, the robot 114, the navigation system 118, the infusion device 126, the database 130, and/or the cloud network 134.

The memory 106 may be or include RAM, DRAM, SDRAM, other solid-state memory, any memory described herein, or any other tangible, non-transitory memory for storing computer-readable data and/or instructions. The memory 106 may store information or data associated with completing, for example, any operation of the methods described herein, or of any other methods. The memory 106 may store, for example, instructions and/or machine learning models that support one or more functions of the computing device 102, the imaging devices 112, the robot 114, the navigation system 118, or the infusion device 126. For instance, the memory 106 may store content (e.g., instructions and/or machine learning models) that, when executed by the processor 104, enable image processing 120, segmentation 122, transformation 124, registration 128, an infusion engine 138, machine learning model(s) 138, and/or processing algorithm(s) 142. Such content, if provided as an instruction, may, in some implementations, be organized into one or more applications, modules, packages, layers, or engines. Alternatively or additionally, the memory 106 may store other types of content or data (e.g., machine learning models, artificial neural networks, deep neural networks, etc.) that can be processed by the processor 104 to carry out the various method and features described herein. Thus, although various contents of memory 106 may be described as instructions, it should be appreciated that functionality described herein can be achieved through use of instructions, algorithms, and/or machine learning models. The data, algorithms, and/or instructions may cause the processor 104 to manipulate data stored in the memory 106 and/or received from or via the imaging devices 112, the robot 114, the navigation system 118, the infusion device 126, the database 130, and/or the cloud network 134.

The computing device 102 may also include a communication interface 108. The communication interface 108 may be used for receiving data or other information from an external source (e.g., the imaging devices 112, the robot 114, the navigation system 118, the database 130, the cloud network 134, and/or any other system or component separate from the system 100), and/or for transmitting instructions, data (e.g., image data, measurements, insertion depth of the infusion device 126, target flow rate associated with the infusion device 126, target withdrawal rate of the infusion device 126, etc.), or other information to an external system or device (e.g., another computing device 102, the imaging devices 112, the robot 114, the navigation system 118, the database 130, the cloud network 134, and/or any other system or component not part of the system 100). The communication interface 108 may include one or more wired interfaces (e.g., a USB port, an Ethernet port, a Firewire port) and/or one or more wireless transceivers or interfaces (configured, for example, to transmit and/or receive information via one or more wireless communication protocols such as 802.11a/b/g/n, Bluetooth, NFC, ZigBee, and so forth). In some implementations, the communication interface 108 may support communication between the device 102 and one or more other processors 104 or computing devices 102, whether to reduce the time needed to accomplish a computing-intensive task or for any other reason.

The computing device 102 may also include one or more user interfaces 110. The user interface 110 may be or include a keyboard, mouse, trackball, monitor, television, screen, touchscreen, and/or any other device for receiving information from a user and/or for providing information to a user. The user interface 110 may be used, for example, to receive a user selection or other user input regarding any operation of any methods described herein. Notwithstanding the foregoing, any required input for any operation of any methods described herein may be generated automatically by the system 100 (e.g., by the processor 104 or another component of the system 100) or received by the system 100 from a source external to the system 100. In some implementations, the user interface 110 may support user modification (e.g., by a surgeon, medical personnel, a patient, etc.) of instructions to be executed by the processor 104 according to one or more implementations of the present disclosure, and/or to user modification or adjustment of a setting of other information displayed on the user interface 110 or corresponding thereto.

In some implementations, the computing device 102 may utilize a user interface 110 that is housed separately from one or more remaining components of the computing device 102. In some implementations, the user interface 110 may be located proximate one or more other components of the computing device 102, while in other implementations, the user interface 110 may be located remotely from one or more other components of the computer device 102.

The imaging device 112 may be operable to image anatomical feature(s) (e.g., a bone, veins, tissue, etc.) and/or other aspects of patient anatomy to yield image data (e.g., image data depicting or corresponding to a bone, veins, tissue, etc.). "Image data" as used herein refers to the data generated or captured by an imaging device 112, including in a machine-readable form, a graphical/visual form, and in any other form. In various examples, the image data may include data corresponding to an anatomical feature of a patient, or to a portion thereof. The image data may be or include a preoperative image, an intraoperative image, a postoperative image, or an image taken independently of any surgical procedure. In some implementations, a first imaging device 112 may be used to obtain first image data (e.g., a first image) at a first time, and a second imaging device 112 may be used to obtain second image data (e.g., a second image) at a second time after the first time. The imaging device 112 may be capable of taking a 2D image or a 3D image to yield the image data. The imaging device 112 may be or include, for example, an ultrasound scanner (which may include, for example, a physically separate transducer and receiver, or a single ultrasound transceiver), an O-arm, a C-arm, a G-arm, or any other device utilizing X-ray-based imaging (e.g., a fluoroscope, a CT scanner, or other X-ray machine), a magnetic resonance imaging (MRI) scanner, an optical coherence tomography (OCT) scanner, an endoscope, a microscope, an optical camera, a thermographic camera (e.g., an infrared camera), a radar system (which may include, for example, a transmitter, a receiver, a processor, and one or more antennae), or any other imaging device 112 suitable for obtaining images of an anatomical feature of a patient. The imaging device 112 may be contained entirely within a single housing, or may include a transmitter/emitter and a receiver/detector that are in separate housings or are otherwise physically separated.

In some implementations, the imaging device 112 may include more than one imaging device 112. For example, a first imaging device may provide first image data and/or a first image, and a second imaging device may provide second image data and/or a second image. In still other implementations, the same imaging device may be used to provide both the first image data and the second image data, and/or any other image data described herein. The imaging device 112 may be operable to generate a stream of image data. For example, the imaging device 112 may be configured to operate with an open shutter, or with a shutter that continuously alternates between open and shut so as to capture successive images. For purposes of the present disclosure, unless specified otherwise, image data may be considered to be continuous and/or provided as an image data stream if the image data represents two or more frames per second.

The robot 114 may be any surgical robot or surgical robotic system. The robot 114 may be or include, for example, the Mazor X™ Stealth Edition robotic guidance system. The robot 114 may be configured to position the imaging device 112 at one or more precise position(s) and orientation(s), and/or to return the imaging device 112 to the same position(s) and orientation(s) at a later point in time. The robot 114 may additionally or alternatively be configured to manipulate a surgical tool (whether based on guidance from the navigation system 118 or not) to accomplish or to assist with a surgical task. In some implementations, the robot 114 may be configured to hold and/or manipulate an anatomical element during or in connection with a surgical procedure. The robot 114 may include one or more robotic arms 116. In some implementations, the robotic arm 116 may include a first robotic arm and a second robotic arm, though the robot 114 may include more than two robotic arms. In some implementations, one or more of the robotic arms 116 may be used to hold and/or maneuver the imaging device 112. In implementations where the imaging device 112 includes two or more physically separate components (e.g., a transmitter and receiver), one robotic arm 116 may hold one such component, and another robotic arm 116 may hold another such component. Each robotic arm 116 may be positionable independently of the other robotic arm. The robotic arms 116 may be controlled in a single, shared coordinate space, or in separate coordinate spaces.

The robot 114, together with the robotic arm 116, may have, for example, one, two, three, four, five, six, seven, or more degrees of freedom. Further, the robotic arm 116 may be positioned or positionable in any pose, plane, and/or focal point. The pose includes a position and an orientation. As a result, an imaging device 112, surgical tool, or other object held by the robot 114 (or, more specifically, by the robotic arm 116) may be precisely positionable in one or more needed and specific positions and orientations.

The robotic arm(s) 116 may include one or more sensors that enable the processor 104 (or a processor of the robot 114) to determine a precise pose in space of the robotic arm (as well as any object or element held by or secured to the robotic arm).

In some implementations, reference markers (e.g., navigation markers) may be placed on the robot 114 (including, e.g., on the robotic arm 116), the imaging device 112, the infusion device 126, a target object 149 later described with reference to FIG. 1B, or any other object in the surgical space. The reference markers may be tracked by the navigation system 118, and the results of the tracking may be used by the robot 114 and/or by an operator of the system 100 or any component thereof. In some implementations, the navigation system 118 can be used to track other components of the system (e.g., imaging device 112) and the system can operate without the use of the robot 114 (e.g., with a surgeon and/or medical technician manually manipulating the imaging device 112, the infusion device 126, and/or one or more surgical tools, based on information and/or instructions generated by the navigation system 118, for example).

The navigation system 118 may provide navigation for a surgeon and/or a surgical robot during an operation. The navigation system 118 may be any now-known or future-developed navigation system, including, for example, the Medtronic StealthStation™ S8 surgical navigation system or any successor thereof. The navigation system 118 may include one or more cameras or other sensor(s) for tracking one or more reference markers, navigated trackers, or other objects within the operating room or other room in which some or all of the system 100 is located. The one or more cameras may be optical cameras, infrared cameras, or other cameras. In some implementations, the navigation system 118 may include one or more electromagnetic sensors. In various implementations, the navigation system 118 may be used to track a position and orientation (e.g., a pose) of the imaging device 112, the robot 114, the robotic arm 116, a target object (e.g., target object 149 later described with reference to FIG. 1B), the infusion device 126, and/or one or more surgical tools (or, more particularly, to track a pose of a navigated tracker attached, directly or indirectly, in fixed relation to the one or more of the foregoing). The navigation system 118 may include a display for displaying one or more images from an external source (e.g., the computing device 102, imaging device 112, or other source) or for displaying an image and/or video stream from the one or more cameras or other sensors of the navigation system 118. In some implementations, the system 100 can operate without the use of the navigation system 118. The navigation system 118 may be configured to provide guidance to a surgeon or other user of the system 100 or a component thereof, to the robot 114, or to any other element of the system 100 regarding, for example, a pose of one or more anatomical elements (e.g., tissue), whether or not a tool (e.g., an infusion device 126) is in the proper trajectory, and/or how to move a tool into the proper trajectory to carry out a surgical task according to a preoperative or other surgical plan.

The infusion device 126 may be a device supportive of performing an infusion of a substance (e.g., a medical substance, a drug, etc.). In some aspects, the infusion device 126 may be a tubular system capable of delivering or leading a fluid (e.g., a liquid, a gas) to a target object 149 later described with reference to FIG. 1A. In some examples, the infusion device 126 may be a catheter or a cannula. The term 'infusion' in the context of this disclosure may encompass the term 'injection.' In some aspects, the fluid may be referred to as a perfusate. The terms 'medical substance,' 'substance,' 'drug,' and 'perfusate' may be used interchangeably herein.

The infusion engine 128 may control infusion of a substance (e.g., a medical substance, a drug, etc.). For example, the infusion engine 128 may control infusion of the substance into a target object, via the robot 114 and the infusion device 126, according to a first flow rate. The infusion engine 128 may set a second flow rate associated with infusing the substance into the target object, based on a withdrawal rate of the infusion device 126 from the target object. The infusion engine 128 may control infusion of the substance into the target object based on the second flow rate.

The processor 104 may utilize data stored in memory 106 as a neural network. The neural network may include a machine learning architecture. In some aspects, the neural network may be or include one or more classifiers. In some other aspects, the neural network may be or include any machine learning network such as, for example, a deep learning network, a convolutional neural network, a reconstructive neural network, a generative adversarial neural network, or any other neural network capable of accomplishing functions of the computing device 102 described herein. Some elements stored in memory 106 may be described as or referred to as instructions or instruction sets, and some functions of the computing device 102 and/or robot 114 may be implemented using machine learning techniques.

For example, the processor 104 may support machine learning model(s) 138 which may be trained and/or updated based on data (e.g., training data 146) provided or accessed by any of the computing device 102, the imaging device 112, the robot 114, the navigation system 118, the infusion device 126, the database 130, and/or the cloud network 134. The machine learning model(s) 138 may be built and updated by the monitoring engine 126 based on the training data 146 (also referred to herein as training data and feedback).

For example, the machine learning model(s) 138 may be trained with one or more training sets included in the training data 146. In some aspects, the training data 146 may include multiple training sets. In an example, the training data 146 may include a first training set that includes infusion rates associated with delivering target volumes of a medical substance (e.g., a drug), via various types of infusion devices 126 (e.g., infusion devices 126 having different respective dimensions). The training data 146 may include a second training set that includes infusion rates associated with delivering target volumes of the medical substance, in association with various approach angles of an infusion device 126 with respect to a target object. The training data 146 may include a third training set that includes withdrawal rates associated with withdrawing an infusion device 126, in association with a property (e.g., viscosity) of the medical substance.

The training data 146 may include a fourth training set that includes withdrawal rates (and changes thereto) associated with withdrawing an infusion device 126, in association with infusion durations and/or delivered volumes of the medical substance.

In some aspects, the neural network may generate additional training sets based on any of the training sets described herein. In some examples, based on the training data 146, the neural network may generate one or more algorithms (e.g., processing algorithms 142) supportive of robotically-assisted drug delivery described herein.

Additional example aspects of the system 100 are later described herein with reference to FIGS. 1B, 2, and 3.

The database 130 may store information that correlates one coordinate system to another (e.g., one or more robotic coordinate systems to a patient coordinate system and/or to a navigation coordinate system). The database 130 may additionally or alternatively store, for example, one or more surgical plans (including, for example, pose information about a target and/or image information about a patient's anatomy at and/or proximate the surgical site) for use by the robot 114, the navigation system 118, and/or a user of the computing device 102 or of the system 100; one or more images useful in connection with a surgery to be completed by or with the assistance of one or more other components of the system 100; and/or any other useful information. The database 130 may additionally or alternatively store, for example, properties (e.g., dimensions, outer diameter, inner diameter, length, etc.) of the infusion device 126 and properties (e.g., viscosity, a prescribed volume, etc.) of a medical substance to be delivered to a patient.

The database 130 may be configured to provide any such information to the computing device 102 or to any other device of the system 100 or external to the system 100, whether directly or via the cloud network 134. In some implementations, the database 130 may include treatment information (e.g., a drug delivery plan, drug dosage information, etc.) associated with a patient. In some implementations, the database 130 may be or include part of a hospital image storage system, such as a picture archiving and communication system (PACS), a health information system (HIS), and/or another system for collecting, storing, managing, and/or transmitting electronic medical records including image data.

In some aspects, the computing device 102 may communicate with a server(s) and/or a database (e.g., database 130) directly or indirectly over a communications network (e.g., the cloud network 134). The communications network may include any type of known communication medium or collection of communication media and may use any type of protocols to transport data between endpoints. The communications network may include wired communications technologies, wireless communications technologies, or any combination thereof.

Wired communications technologies may include, for example, Ethernet-based wired local area network (LAN) connections using physical transmission mediums (e.g., coaxial cable, copper cable/wire, fiber-optic cable, etc.). Wireless communications technologies may include, for example, cellular or cellular data connections and protocols (e.g., digital cellular, personal communications service (PCS), cellular digital packet data (CDPD), general packet radio service (GPRS), enhanced data rates for global system for mobile communications (GSM) evolution (EDGE), code division multiple access (CDMA), single-carrier radio transmission technology (1×RTT), evolution-data optimized (EVDO), high speed packet access (HSPA), universal mobile telecommunications service (UMTS), 3G, long term evolution (LTE), 4G, and/or 5G, etc.), Bluetooth®, Bluetooth® low energy, Wi-Fi, radio, satellite, infrared connections, and/or ZigBee® communication protocols.

The Internet is an example of the communications network that constitutes an Internet Protocol (IP) network consisting of multiple computers, computing networks, and other communication devices located in multiple locations, and components in the communications network (e.g., computers, computing networks, communication devices) may be connected through one or more telephone systems and other means. Other examples of the communications network may include, without limitation, a standard Plain Old Telephone System (POTS), an Integrated Services Digital Network (ISDN), the Public Switched Telephone Network (PSTN), a Local Area Network (LAN), a Wide Area Network (WAN), a wireless LAN (WLAN), a Session Initiation Protocol (SIP) network, a Voice over Internet Protocol (VoIP) network, a cellular network, and any other type of packet-switched or circuit-switched network known in the art. In some cases, the communications network 120 may include of any combination of networks or network types. In some aspects, the communications network may include any combination of communication mediums such as coaxial cable, copper cable/wire, fiber-optic cable, or antennas for communicating data (e.g., transmitting/receiving data).

The computing device 102 may be connected to the cloud network 134 via the communication interface 108, using a wired connection, a wireless connection, or both. In some implementations, the computing device 102 may communicate with the database 130 and/or an external device (e.g., another computing device, the robot 114, etc.) via the cloud network 134. In some aspects, the computing device 102 may be electronically coupled to and/or integrated with the robot 114.

The system 100 or similar systems may be used, for example, to carry out one or more aspects of any of the process flow 200 and process flow 300 described herein. The system 100 or similar systems may also be used for other purposes.

Figure 1B:
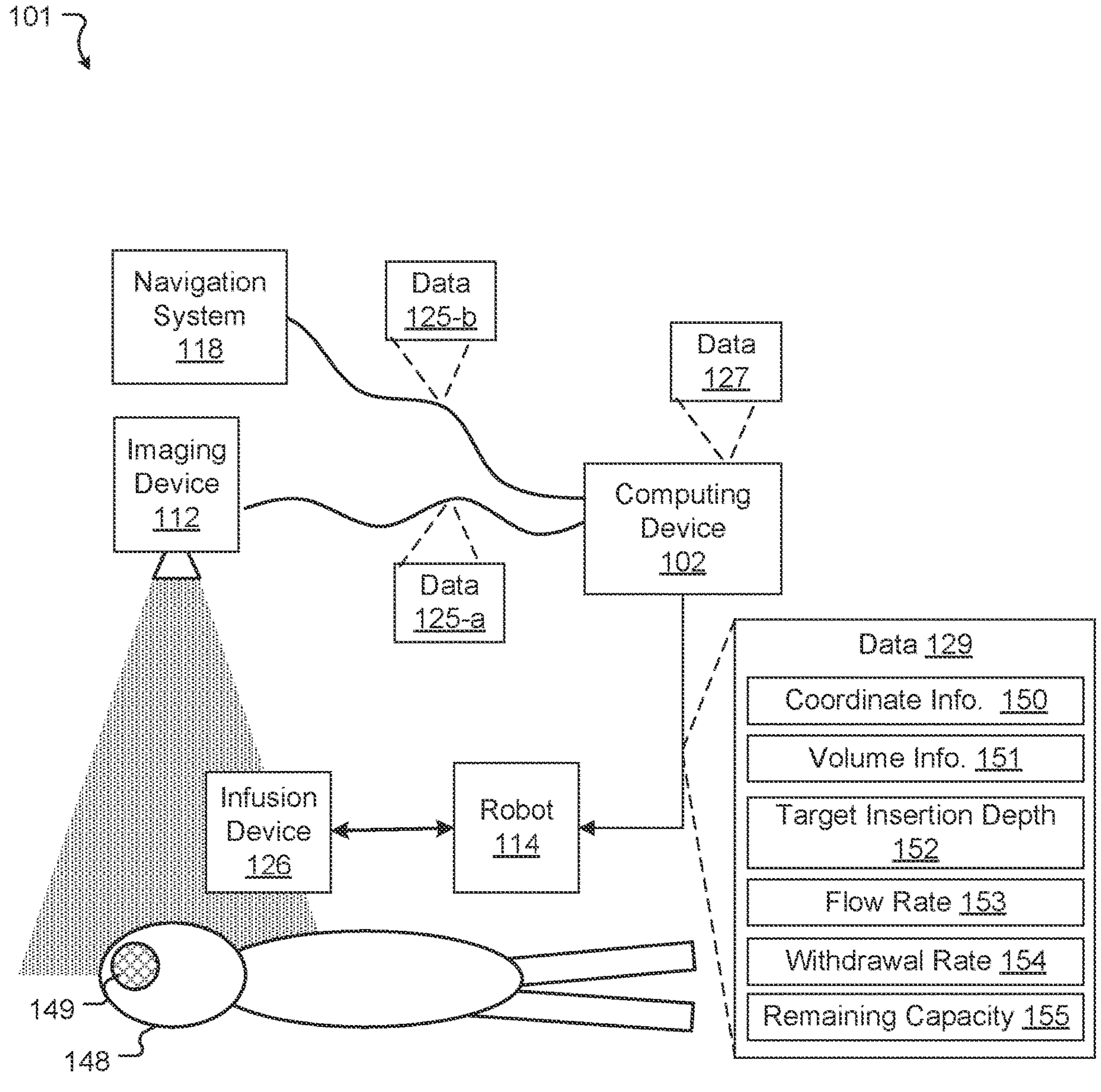

FIG. 1B illustrates an example 101 of the system 100 that supports aspects of the present disclosure. As described herein, the system 100 supports robotic robotically-assisted drug delivery to a patient.

In an example, the imaging device 112 may provide data 125-*a* associated with a subject 148 (e.g., a patient) to the computing device 102. The data 125-*a* may include, for example, image data (also referred to herein as 'imaging data') of a region of interest of the subject 148. For example, the region of interest may include a target object 149 (or portion thereof) and an infusion device 126 (or portion thereof).

In another example, the navigation system 118 may provide data 125-*b* associated with the subject 148 to the computing device 102. The data 125-*b* may include, for example, sensor information, coordinate information, pose data, guidance data, and/or tracking data as described herein with reference to the navigation system 118. The data 125-*a* and the data 125-*b* may collectively be referred to herein as the data 125.

The target object 149 may be an anatomical element (e.g., brain, brain tissue, other cellular tissue, etc.) of the subject 149. Based on the data 125 (e.g., image data, pose data, etc.), the computing device 102 may calculate coordinate information 150 (e.g., real-time or near real-time coordinates) associated with the infusion device 126 and/or target object 149. Additionally, or alternatively, the navigation system 118 may calculate and provide the coordinate information 150 to the computing device 102 and/or robot 114. In some aspects, using the data 125 (e.g., image data), the computing device 102 may calculate volume information 151 (e.g., a volume) of the target object 149.

Using the data 125, the computing device 102 may calculate parameters associated with inserting the infusion device 126 into the target object 149. For example, the parameters may include a target location (e.g., coordinates) at the target object 149 to insert the infusion device 126. In some other aspects, the parameters may include a target approach angle of the infusion device 126 with respect to the target object 149. For example, the computing device 102 may calculate an approach angle for inserting the infusion device 126 into the target object 149. In an example, the computing device 102 may calculate the target location (e.g., coordinates) and target approach angle in association with achieving a target fill (e.g., optimal fill) of the target object 149.

The computing device 102 may calculate a target insertion depth 152 of inserting the infusion device 126 with respect to the target object 149. For example, using the data 125, the computing device 102 may determine the target insertion depth 152 of the infusion device 126 with respect to the target object 149. Additionally, or alternatively, using the data 125 (e.g., image data, tracking data, etc.), the computing device 102 may determine an actual insertion depth of the infusion device 126 at any temporal instance.

In another example, the computing device 102 may set a flow rate 153 associated with infusing a substance (e.g., a drug, etc.) into the target object 149. For example, the computing device 102 may set the flow rate (e.g., a first flow rate) based on the insertion depth of the infusion device 126. Additionally, or alternatively, the computing device 102 may set the flow rate (e.g., first flow rate) based on one or more dimensions of the infusion device 126. For example, the infusion device 126 may be a cannula, and the computing device 102 may set the flow rate based on an outer diameter and/or inner diameter of the infusion device 126. In some cases, the computing device 102 may set the flow rate (e.g., first flow rate) based on the target approach angle. The terms 'infusion rate' and 'flow rate' may be used interchangeably herein.

Accordingly, for example, the computing device 102 may set the flow rate based on the insertion depth of the infusion device 126, one or more dimensions of the infusion device 126, and/or the target approach angle. The computing device 102 may further adjust the flow rate at any temporal instance, examples of which described herein.

According to example aspects of the present disclosure, the computing device 102 may infuse the substance into the target object 149 via the infusion device 126, based on the flow rate 153 and a withdrawal rate 154. The computing device 102 may calculate the withdrawal rate 154 based on one or more properties (e.g., viscosity, diffusion coefficient, concentration, etc.) associated with the substance. For example, the computing device 102 may set a relatively higher withdrawal rate 154 for a substance having a relatively lower viscosity. In another example, the computing device 102 may set a relatively lower withdrawal rate 154 for a substance having a relatively higher viscosity. Other example properties of the substance, based on which the computing device 102 may calculate the withdrawal rate 154 include pressure, fluid resistance, and density of the substance, but are not limited thereto.

The computing device 102 may calculate a remaining capacity 155 included in the volume of the target object 149. The computing device 102 may calculate the remaining capacity 155 based on the volume information 151, the withdrawal rate 154, temporal information (e.g., elapsed duration of a procedure), and/or one or more dimensions (e.g., outer diameter, inner diameter, length, etc.) of the infusion device 126.

The computing device 102 may adjust the flow rate 153 (e.g., set a second flow rate) at any temporal instance. For example, the computing device 102 may adjust the flow rate 153 based on the withdrawal rate 154 and the remaining capacity 155. The computing device 102 may infuse the substance into the target object 149 based on adjusting the flow rate 153.

The computing device 102 may electronically transmit data 129 to the robot 114 to the robot 114 in a data format compatible with the robot 114. The data 129 may include information described herein (e.g., coordinate information 150, volume information 151, target insertion depth 152, flow rate 153, withdrawal rate 154, remaining capacity 155, etc.) and changes thereto. The data 129 may include instructions associated with delivering the medical substance to the subject 148. Using the data 129, the robot 114 may control a robotic arm 116 in association with delivering the medical substance to the subject 148. For example, the robot 114 may control the robotic arm 116 (e.g., control speed, rotation, etc.) in association with inserting the infusion device 126 into and withdrawing the infusion device 126 from the target object 149, according to the data 129.

According to example aspects of the present disclosure, the computing device 102 may calculate and/or set any parameter value (e.g., coordinate information 150, volume information 151, target insertion depth 152, flow rate 153, withdrawal rate 154, etc.) described herein, at any temporal instance. For example, the computing device 102 may calculate, set, and adjust values of any parameters described herein (e.g., coordinate information 150, volume information 151, target insertion depth 152, flow rate 153, withdrawal rate 154, remaining capacity 155, etc.), prior to and/or during a medical procedure. Examples of the parameters and respective values thereof are later described with reference to FIG. 2.

Aspects of the present disclosure support implementing aspects of the system 100 using machine learning model 138 (e.g., described with reference to FIG. 1A). For example, the computing device 102 may provide the data 125 (e.g., data 125-*a*, data 125-*b*) and/or data 127 (e.g., one or more properties associated with the medical substance, one or more properties associated with the infusion device 126, etc.) to machine learning model 138. The computing device 102 may receive an output from the machine learning model 128 in response to the machine learning model 128 processing the data 125 (or a portion thereof) and/or the data 127 (or a portion thereof). The output may include the data 129 (or a portion thereof). For example, the output may include one or more values of the parameters described herein (e.g., coordinate information 150, volume information 151, target insertion depth 152, flow rate 153, withdrawal rate 154, etc.).

Aspects of the present disclosure support processing of the data 125 and/or the data 127, and generation of the data 129, based on one or more criteria. For example, the computing device 102 may process the data 125 and/or the data 127 and generate the data 129 based on a temporal schedule (e.g., periodically, semi-periodically). In some cases, the computing device 102 may process the data 125 and/or the data 127 and generate the data 129 based on a trigger condition (e.g., updates to any of the data 125 and/or the data 127). In some other cases, the computing device 102 may regenerate a portion (e.g., flow rate 153, withdrawal rate 154, etc.) of the data 129 based on changes to another portion (e.g., remaining capacity 155) of the data 129.

In some cases, the computing device 102 may process the data 125 and/or the data 127 and generate the data 129 until one or more criteria are satisfied. For example, the computing device 102 may adjust the flow rate 153 and/or withdrawal rate 154 until an entire prescribed volume of the medical substance is delivered to the target object 149 (e.g., infused into the target object 149).

Figure 2:
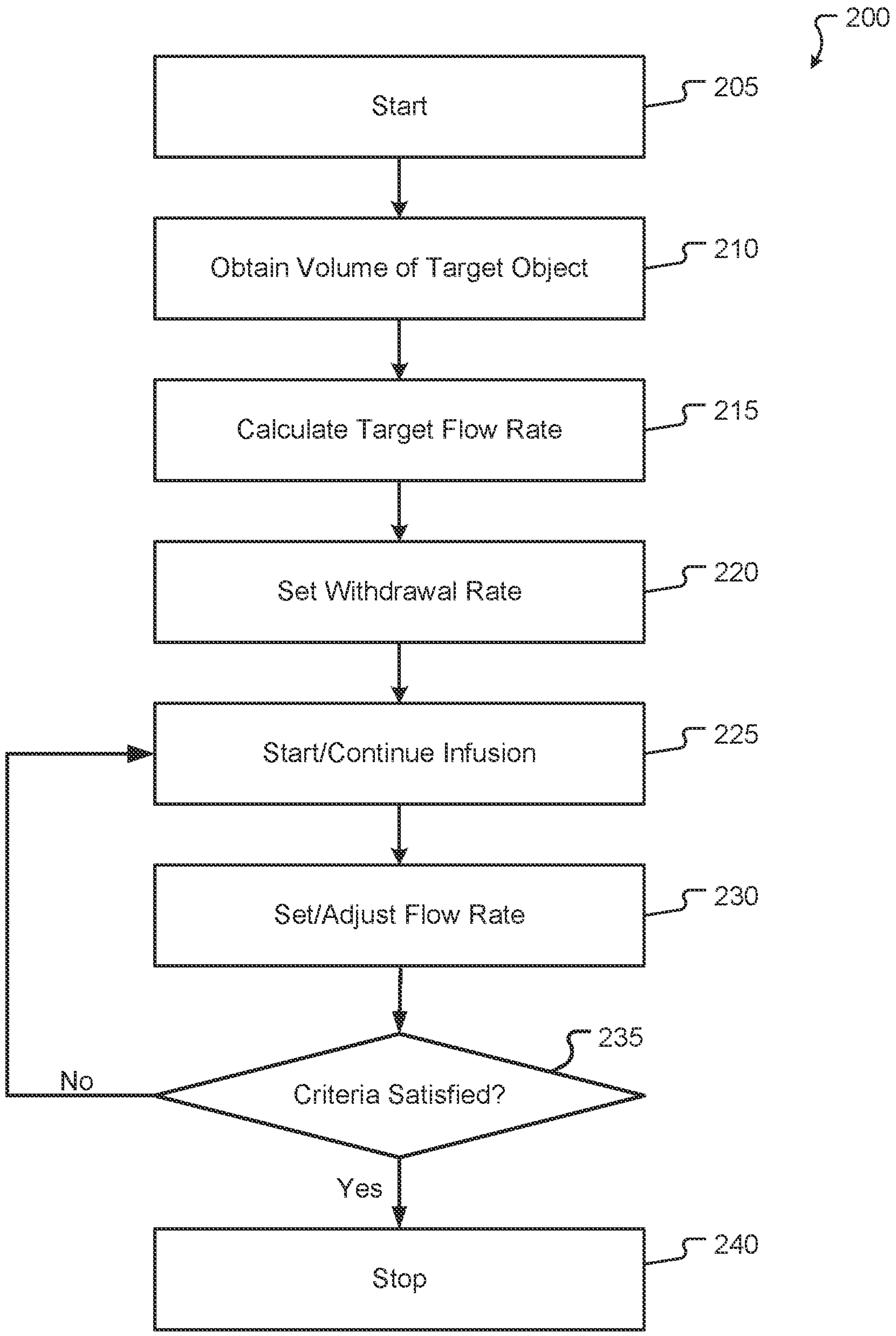
FIG. 2 illustrates an example of a process flow that supports aspects of the present disclosure.

FIG. 2 illustrates an example of a process flow 200 that supports robotically-assisted drug delivery to a patient in accordance with aspects of the present disclosure. In some examples, process flow 200 may be implemented by a system 100 described with reference to FIGS. 1A and 1B.

Aspects of the process flow 200 support achieving an optimal infusion by the system 100. For example, aspects of the process flow 200 support achieving target infusion rate, target infusion duration, target infusion volume, target coverage area, etc. for a target object 149. With reference to example 101 of FIG. 1B, the process flow 200 may include receiving, as an input, a volume (e.g., volume information 151) of the target object 149 to be infused. The terms 'target object' and 'target structure' may be used interchangeably herein.

The process flow 200 may include adjusting an infusion rate (e.g., flow rate 153) that matches the intake capacity, at the volume, for a medical substance (e.g., perfusate) as the infusion device 126 is withdrawn. In some cases, the computing device 102 may automatically extract the volume of the target object 149 based on imaging data provided by the imaging device 112. In an example, the computing device 102 may process the image data using one or more image processing techniques (e.g., standard image processing approaches).

In some aspects, the computing device 102 may receive input data from a user (e.g., via user interface 110, via another computing device 102, etc.), and the input data may include the volume of the target object 149. Additionally, or alternatively, the computing device 102 may support a combination of extracting the volume based on processed data and receiving input data indicating the volume. For example, the computing device 102 may automatically extract the volume. The extracted volume may be reviewed by a user (e.g., medical personnel) in association with ensuring accuracy of the volume and/or adjusting the value thereof.

The computing device 102 may extract and/or receive additional parameters in association with setting and adjusting the infusion rate (e.g., flow rate 153). For example, the computing device 102 may automatically extract parameters from the system 100 in association with adjusting the infusion rate for optimal infusion. Examples of extracted parameters include outer and inner diameters of the infusion device 126, withdrawal rate 154 of the infusion device 126, and length of the overall withdrawal, but are not limited thereto. Additionally, or alternatively, the computing device 102 may receive input data including any combination of the parameters. As described herein, aspects of the process flow 200 support using the volume of the target object 149 and other system component variables as input to estimate a target infusion rate.

An example implementation is now described with reference to process flow 200. In the following description of the process flow 200, the operations may be performed in a different order than the order shown, or the operations may be performed in different orders or at different times. Certain operations may also be left out of the process flow 200, or other operations may be added to the process flow 200.

It is to be understood that while a computing device 102 (e.g., infusion engine 128) is described as performing a number of the operations of process flow 200, any device (e.g., another computing device 102 in communication with the computing device 102, a robot 114, etc.) may perform the operations shown.

At 205, the computing device 102 and/or robot 114 may start or initiate the process flow 200.

At 210, the process flow 200 may include obtaining the volume of a target object 149 to be infused. For example, at 210, the computing device 102 may obtain, as input, the volume of the target object 149. The computing device 102 may automatically extract the volume and/or receive input data (e.g., by a user) indicating the volume.

In some alternative and/or additional aspects, at 210, the computing device 102 may automatically obtain coordinate information 150 (e.g., coordinates, pose, etc.) of the target object 149 and/or receive input data (e.g., from the navigation system 118, from a user, etc.) indicating the coordinate information 150.

At 215, the process flow 200 may include calculating a target flow rate (e.g., estimate an optimal infusion rate) associated with infusing a substance into the target object 149. For example, at 215, the computing device 102 may obtain one or more parameters in association with calculating or estimating the target flow rate. Example parameters include one or more properties of the infusion device 126 (e.g., an outer diameter of the infusion device 126, an inner diameter of the infusion device 126, a length of the infusion device 126, etc.) and an approach angle of the infusion device 126 with respect to the target object 149, but are not limited thereto. The computing device 102 may calculate the target flow rate based on one or more of the parameters.

At 220, the process flow 200 may include setting the withdrawal rate 154 (e.g., a target or optimal withdrawal rate). For example, at 220, the computing device 102 may automatically set the withdrawal rate 154 based on properties (e.g., viscosity, etc.) of the substance. Additionally, or alternatively, at 220, the computing device 102 may estimate total infusion time based on one or more properties (e.g., viscosity, etc.) of the substance.

In some aspects, the system 100 may support user-based adjustments to the withdrawal rate 154. For example, the computing device 102 may receive user inputs for adjusting the withdrawal rate 154. In an example, the computing device 102 may receive a user input for adjusting the withdrawal rate 154 if the user determines that the perfusion time is extraordinarily long (e.g., exceeding a threshold temporal duration). In some other cases, the computing device 102 may adjust the withdrawal rate 154 based on the threshold temporal duration. For example, the computing device 102 may increase the withdrawal rate for cases in which the computing device 102 determines that an elapsed perfusion duration exceeds the threshold temporal duration.

At 225, the process flow 200 may include starting an infusion process. For example, at 225, the computing device 102 may initiate delivery (e.g., infusion) of the medical substance and withdrawal of the infusion device 126. Additionally, at 225, the computing device 102 may continue the infusion process (e.g., continue delivery of the medical substance, continue withdrawal of the infusion device 126) in response to a 'No' decision, aspects of which are later described herein with reference to 235.

At 230, the process flow 200 may include setting and/or adjusting the flow rate associated with delivering the medical substance to the target object 149. For example, at 230, the computing device 102 may maintain or adjust the flow rate calculated at 215. In an example, the computing device 102 may adjust the flow rate based on one or more properties of the infusion device 126 (e.g., an outer diameter of the infusion device 126, an inner diameter of the infusion device 126, a length of the infusion device 126, etc.), the withdrawal rate set at 220, and/or a remaining capacity included in the volume of the target object 149. The remaining capacity may correspond to, for example, a cavity left behind by the infusion device 126 in the volume of the target object 149.

In some examples, the computing device 102 may calculate the remaining capacity based on the withdrawal rate of the infusion device 126, a dimension (e.g., outer diameter) of the infusion device 126, and/or an elapsed infusion duration. Additionally, or alternatively, the computing device 102 may calculate the remaining capacity based on updated image data (e.g., inclusive of image data of the infusion device 126 and/or the target object 149) provided by the imaging device 112. Additionally, or alternatively, the computing device 102 may determine the remaining capacity based on a user input.

Accordingly, for example, at 230, the computing device 102 may match automatic infusion to fill a cavity left behind by the infusion device 126. In an example, for a withdrawal rate of 1 mm/minute and an infusion device 126 having an outer diameter of 500 μm, the computing device 102 may set a flow rate of about 0.8 $mm^3$/minute.

At 235, the process flow 200 may include determining whether to continue or discontinue delivering the medical substance to the target object 149. For example, at 235, the process flow 200 may include identifying whether one or more criteria has been satisfied. The process flow 200 may include returning to 225 (e.g., 'Continue Infusion') or proceeding to 240 (e.g., 'Stop') based on whether the one or more criteria has been satisfied. The one or more criteria may be associated with delivery of the medical substance to the target object 149. Some examples of the criteria are described below.

In an example, at 235, the computing device 102 (and/or robot 114) may determine whether an entire allocated volume of the medical substance has been fully delivered to the target object 149. For example, if the computing device 102 determines that the robot 114 has delivered the entire allocated volume of the medical substance to the target object 149 (e.g., Criteria Satisfied='Yes'), the computing device 102 may electronically transmit instructions to the robot 114, instructing the robot 114 to discontinue delivering the medical substance (e.g., the process flow 200 proceeds to 240 ('Stop')). In some additional and/or alternative aspects, the robot 114 may determine that the robot 114 has delivered the entire allocated volume of the medical substance to the target object 149 (e.g., Criteria Satisfied='Yes'), and the robot 114 may discontinue delivering the medical substance (e.g., the process flow 200 proceeds to 240 ('Stop')).

In another example, at 235, if the computing device 102 determines that the robot 114 has not yet delivered the entire allocated volume of the medical substance to the target object 149 (e.g., Criteria Satisfied='No'), the computing device 102 may return to 225 (e.g., 'Continue Infusion'), 230 ('Adjust Flow Rate'), and 235 ('Criteria Satisfied?'). In some additional and/or alternative aspects, the robot 114 may determine that the robot 114 has not yet delivered the entire allocated volume of the medical substance to the target object 149 (e.g., Criteria Satisfied='No'), and the robot 114 may electronically transmit data to the computing device 102. In an example, the data may include an indication that the entire allocated volume has not yet been delivered, and the computing device 102 may return to 225 (e.g., 'Continue Infusion'), 230 ('Adjust Flow Rate'), and 235 ('Criteria Satisfied?'). In another example, the data may include an indication of the remaining volume of the medical substance to be delivered. Based on the data, the computing device 102 may return to 225 (e.g., 'Continue Infusion'), 230 ('Adjust Flow Rate'), and 235 ('Criteria Satisfied?').

In an example implementation, following a 'No' result at 235, the computing device 102 may return to 225 (e.g., 'Continue Infusion'). At 225, the computing device 102 may calculate the remaining capacity included in the volume of the target object 149. In an example, the computing device 102 may calculate the remaining capacity based on the withdrawal rate 154 of the infusion device 126, a dimension (e.g., outer diameter, length, etc.) of the infusion device 126, and/or an elapsed infusion duration. Additionally, or alternatively, the computing device 102 may calculate the remaining capacity based on updated image data provided by the imaging device 112 and/or updated coordinate information provided by the navigation system 118. Additionally, or alternatively, the computing device 102 may determine the remaining capacity based on a user input.

Figure 3:
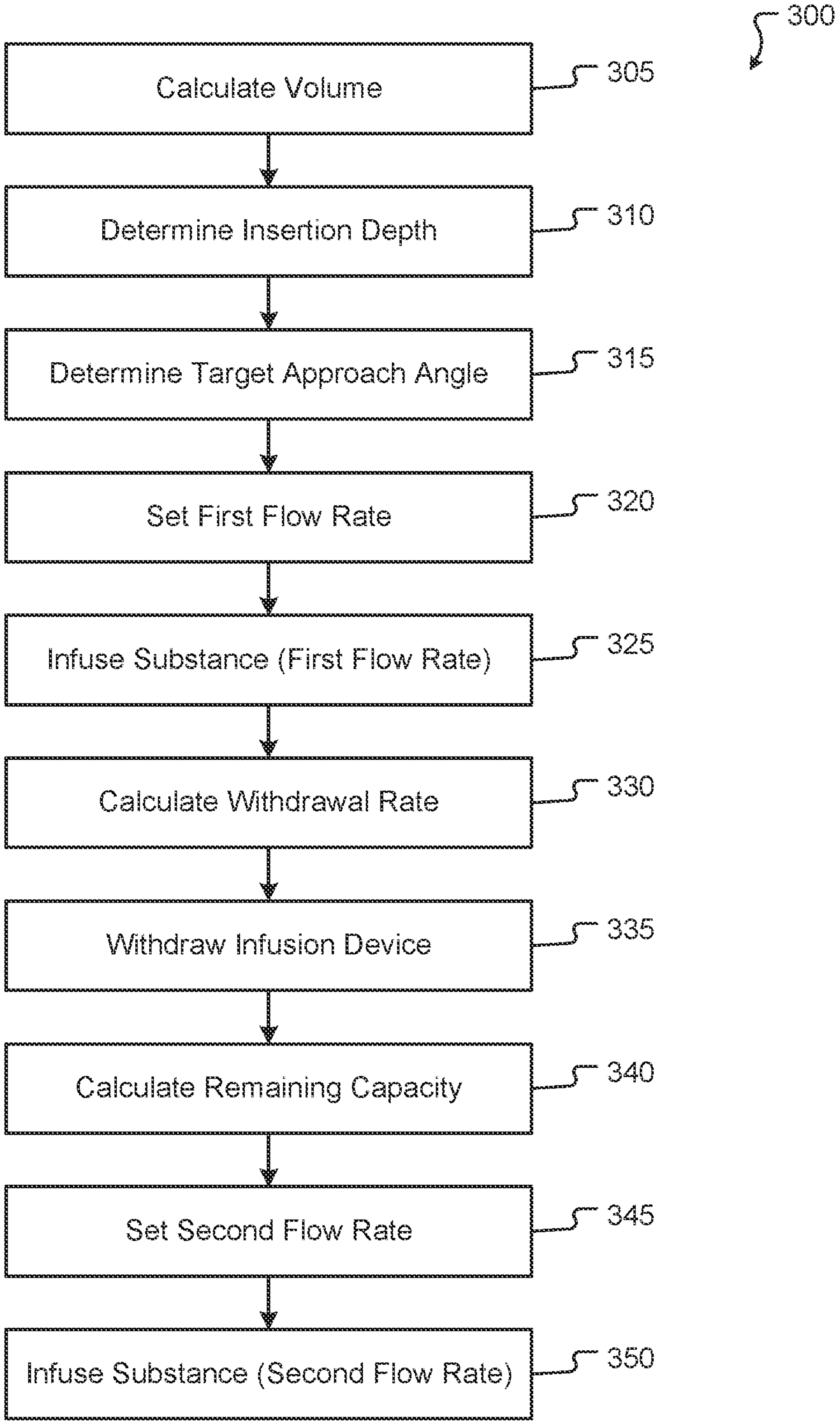
FIG. 3 illustrates an example of a process flow that supports aspects of the present disclosure.

FIG. 3 illustrates an example of a process flow 300 that supports robotically-assisted drug delivery to a patient in accordance with aspects of the present disclosure. In some examples, process flow 300 may implement aspects of the system 100 described with reference to FIGS. 1A and 1B.

In the following description of the process flow 300, the operations may be performed in a different order than the order shown, or the operations may be performed in different orders or at different times. Certain operations may also be left out of the process flow 300, or other operations may be added to the process flow 300.

It is to be understood that while a computing device 102 and/or a robot 114 may perform a number of the operations of process flow 300, any device (e.g., another computing device 102 in communication with the computing device 102, a robot 114, etc.) may perform the operations shown.

At 305, the process flow 300 may include calculating a volume of a target object based on image data including the target object.

At 310, the process flow 300 may include determining an insertion depth of an infusion device with respect to the target object, based on the image data including the target object.

At 315, the process flow 300 may include determining a target approach angle of the infusion device with respect to the target object, based on the image data including the target object.

At 320, the process flow 300 may include setting a first flow rate based on determining the insertion depth. In some aspects, the process flow 300 may include setting the first flow rate based on one or more dimensions of the infusion device. Additionally, or alternatively, at 320, the process flow 300 may include setting the first flow rate based on the target approach angle.

At 325, the process flow 300 may include infusing a substance into the target object, via the infusion device, according to the first flow rate.

At 330, the process flow 300 may include calculating the withdrawal rate based on one or more properties associated with the substance.

At 335, the process flow 300 may include withdrawing the infusion device based on the withdrawal rate.

At 340, the process flow 300 may include calculating a remaining capacity included in the volume of the target object, based on the withdrawal rate and the one or more dimensions of the infusion device.

At 345, the process flow 300 may include setting a second flow rate associated with infusing the substance into the target object, based on the withdrawal rate of the infusion device from the target object. In some aspects, setting the second flow rate may be based on calculating the remaining capacity included in the volume of the target object.

At 350, the process flow 300 may include infusing the substance into the target object based on the second flow rate.

In some aspects (not illustrated), the process flow 300 may include comparing an elapsed duration associated with infusing the substance to a temporal threshold; and adjusting the withdrawal rate based on a result of the comparison.

In some example implementations (not illustrated), the process flow 300 may include providing to a machine learning model, at least one of: image data including the target object and the infusion device; one or more properties associated with the substance; and one or more properties associated with the infusion device. The process flow 300 may include receiving an output from the machine learning model in response to the machine learning model processing at least one of the image data, the one or more properties associated with the substance, and the one or more properties associated with the infusion device, wherein the output includes one or more parameters associated with infusing the substance into the target object.

In some example implementations, the process flow 300 may include repeating one or more operations until one or more criteria are satisfied. For example, the process flow 300 may include one or more iterations of any of 330 through 350 until an entire prescribed volume of a medical substance is delivered to a target object (e.g., infused into an anatomical element of a patient).

In the following description of the process flow 300, the operations may be performed in a different order than the order shown, or the operations may be performed in different orders or at different times. Certain operations may also be left out of the process flow 300, or other operations may be added to the process flow 300.

The process flows 200 and 300 (and/or one or more operations thereof) described herein may be carried out or otherwise performed, for example, by at least one processor. The at least one processor may be the same as or similar to the processor(s) 104 of the computing device 102 described above. The at least one processor may be part of a robot (such as a robot 114) or part of a navigation system (such as a navigation system 118). A processor other than any processor described herein may also be used to execute the process flow 400. The at least one processor may perform operations of the process flow 400 by executing elements stored in a memory such as the memory 106. The elements stored in memory and executed by the processor may cause the processor to execute one or more operations of a function as shown in the process flow 400. One or more portions of the process flow 400 may be performed by the processor executing any of the contents of memory, such as image processing 120, segmentation 122, transformation 124, registration 128, and/or infusion engine 138.

As noted above, the present disclosure encompasses methods with fewer than all of the operations identified in FIGS. 2 and 3 (and the corresponding description of the process flows 200 and 300), as well as methods that include additional operations beyond those identified in FIGS. 2 and 3 (and the corresponding description of the process flows 200 and 300). The present disclosure also encompasses methods that include one or more operations from one method described herein, and one or more operations from another method described herein. Any correlation described herein may be or include a registration or any other correlation.

The foregoing is not intended to limit the disclosure to the form or forms disclosed herein. In the foregoing Detailed Description, for example, various features of the disclosure are grouped together in one or more aspects, implementations, and/or configurations for the purpose of streamlining the disclosure. The features of the aspects, implementations, and/or configurations of the disclosure may be combined in alternate aspects, implementations, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, implementation, and/or configuration. Thus, the following claims are hereby incorporated into this Detailed Description, with each claim standing on its own as a separate preferred implementation of the disclosure.

Moreover, though the foregoing has included description of one or more aspects, implementations, and/or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, implementations, and/or configurations to the extent permitted, including alternate, interchangeable and/or equivalent structures, functions, ranges or operations to those claimed, whether or not such alternate, interchangeable and/or equivalent structures, functions, ranges or operations are disclosed herein, and without intending to publicly dedicate any patentable subject matter.

Example aspects of the present disclosure include:

A system including: a processor; and a memory storing instructions thereon that, when executed by the processor, cause the processor to: infuse a substance into a target object, via an infusion device, according to a first flow rate; set a second flow rate associated with infusing the substance into the target object, based on a withdrawal rate of the infusion device from the target object; and infuse the substance into the target object based on the second flow rate.

Any of the aspects herein, wherein setting the second flow rate is based on calculating a remaining capacity included in a volume of the target object.

Any of the aspects herein, wherein the instructions are further executable by the processor to: calculate the remaining capacity based on the withdrawal rate and one or more dimensions of the infusion device.

Any of the aspects herein, wherein the instructions are further executable by the processor to: calculate the withdrawal rate based on one or more properties associated with the substance; and withdraw the infusion device based on the withdrawal rate.

Any of the aspects herein, wherein the instructions are further executable by the processor to: compare an elapsed duration associated with infusing the substance to a temporal threshold; and adjust the withdrawal rate based on a result of the comparison.

Any of the aspects herein, wherein the instructions are further executable by the processor to: calculate a volume of the target object based on image data including the target object.

Any of the aspects herein, wherein the instructions are further executable by the processor to: determine an insertion depth of the infusion device with respect to the target object, based on image data including the target object; and setting the first flow rate based on: determining the insertion depth; and one or more dimensions of the infusion device.

Any of the aspects herein, wherein the instructions are further executable by the processor to: determine a target approach angle of the infusion device with respect to the target object, based on image data including the target object; and set the first flow rate based on the target approach angle.

Any of the aspects herein, wherein the instructions are further executable by the processor to: provide to a machine learning model, at least one of: image data including the target object and the infusion device; one or more properties associated with the substance; and one or more properties associated with the infusion device; and receive an output from the machine learning model in response to the machine learning model processing at least one of the image data, the one or more properties associated with the substance, and the one or more properties associated with the infusion device, wherein the output includes one or more parameters associated with infusing the substance into the target object.

Any of the aspects herein, wherein the one or more parameters include: the withdrawal rate; the first flow rate; and the second flow rate.

A system including: an infusion device; a processor; and a memory storing data thereon that, when processed by the processor, cause the processor to: infuse a substance into a target object, via the infusion device, according to a first flow rate; set a second flow rate associated with infusing the substance into the target object, based on a withdrawal rate of the infusion device from the target object; and infuse the substance into the target object based on the second flow rate.

Any of the aspects herein, wherein setting the second flow rate is based on calculating a remaining capacity included in a volume of the target object.

Any of the aspects herein, wherein the instructions are further executable by the processor to: calculate the remaining capacity based on the withdrawal rate and one or more dimensions of the infusion device.

Any of the aspects herein, wherein the instructions are further executable by the processor to: calculate the withdrawal rate based on one or more properties associated with the substance; and withdraw the infusion device based on the withdrawal rate.

Any of the aspects herein, wherein the instructions are further executable by the processor to: compare an elapsed duration associated with infusing the substance to a temporal threshold; and adjust the withdrawal rate based on a result of the comparison.

Any of the aspects herein, wherein the instructions are further executable by the processor to: calculate a volume of the target object based on image data including the target object.

Any of the aspects herein, wherein the instructions are further executable by the processor to: determine an insertion depth of the infusion device with respect to the target object, based on image data including the target object; and setting the first flow rate based on: determining the insertion depth; and one or more dimensions of the infusion device.

Any of the aspects herein, wherein the instructions are further executable by the processor to: determine a target approach angle of the infusion device with respect to the target object, based on image data including the target object; and set the first flow rate based on the target approach angle.

Any of the aspects herein, wherein the instructions are further executable by the processor to: provide to a machine learning model, at least one of: image data including the target object and the infusion device; one or more properties associated with the substance; and one or more properties associated with the infusion device; and receive an output from the machine learning model in response to the machine learning model processing at least one of the image data, the one or more properties associated with the substance, and the one or more properties associated with the infusion device, wherein the output includes one or more parameters associated with infusing the substance into the target object.

A method including: infusing a substance into a target object, via an infusion device, according to a first flow rate; setting a second flow rate associated with infusing the substance into the target object, in response to determining a withdrawal rate associated with withdrawing the infusion device from the target object; and infusing the substance into the target object based on the second flow rate.

Any of the aspects herein, wherein setting the second flow rate is based on calculating a remaining capacity included in a volume of the target object.

Any of the aspects herein, further including: calculating the remaining capacity based on the withdrawal rate and one or more dimensions of the infusion device.

Any of the aspects herein, further including: calculating the withdrawal rate based on one or more properties associated with the substance; and withdrawing the infusion device based on the withdrawal rate.

Any of the aspects herein, further including: comparing an elapsed duration associated with infusing the substance to a temporal threshold; and adjusting the withdrawal rate based on a result of the comparison.

Any of the aspects herein, further including: calculating a volume of the target object based on image data including the target object.

Any of the aspects herein, further including: determining an insertion depth of the infusion device with respect to the target object, based on image data including the target object; and setting the first flow rate based on: determining the insertion depth; and one or more dimensions of the infusion device.

Any of the aspects herein, further including: determining a target approach angle of the infusion device with respect to the target object, based on image data including the target object; and setting the first flow rate based on the target approach angle.

Any of the aspects herein, further including: providing to a machine learning model, at least one of: image data including the target object and the infusion device; one or more properties associated with the substance; and one or more properties associated with the infusion device; and receiving an output from the machine learning model in response to the machine learning model processing at least one of the image data, the one or more properties associated with the substance, and the one or more properties associated with the infusion device, wherein the output includes one or more parameters associated with infusing the substance into the target object.

A system, including: an infusion device; a robot device; infusion management circuitry that controls infusion of a substance by: infusing the substance into a target object, via the robot device and the infusion device, according to a first flow rate; setting a second flow rate associated with infusing the substance into the target object, based on a withdrawal rate of the infusion device from the target object; and infusing the substance into the target object based on the second flow rate.

Any of the aspects herein, wherein: the infusion management circuitry calculates a remaining capacity included in a volume of the target object; and setting the second flow rate is based on calculating the remaining capacity.

Any of the aspects herein, wherein: the infusion management circuitry calculates the remaining capacity based on the withdrawal rate and one or more dimensions of the infusion device.

Any of the aspects herein, wherein: the infusion management circuitry calculates the withdrawal rate based on one or more properties associated with the substance; and the robot device withdraws the infusion device based on the withdrawal rate.

A non-transitory computer readable medium including instructions, which when executed by a processor: infuse a substance into a target object, via an infusion device, according to a first flow rate; set a second flow rate associated with infusing the substance into the target object, based on a withdrawal rate of the infusion device from the target object; and infuse the substance into the target object based on the second flow rate.

Any aspect in combination with any one or more other aspects.

Any one or more of the features disclosed herein.

Any one or more of the features as substantially disclosed herein.

Any one or more of the features as substantially disclosed herein in combination with any one or more other features as substantially disclosed herein.

Any one of the aspects/features/implementations in combination with any one or more other aspects/features/implementations.

Use of any one or more of the aspects or features as disclosed herein.

It is to be appreciated that any feature described herein can be claimed in combination with any other feature(s) as described herein, regardless of whether the features come from the same described implementation.

The phrases "at least one," "one or more," "or," and "and/or" are open-ended expressions that are both conjunctive and disjunctive in operation. For example, each of the expressions "at least one of A, B and C," "at least one of A, B, or C," "one or more of A, B, and C," "one or more of A, B, or C," "A, B, and/or C," and "A, B, or C" means A alone, B alone, C alone, A and B together, A and C together, B and C together, or A, B and C together.

The term "a" or "an" entity refers to one or more of that entity. As such, the terms "a" (or "an"), "one or more," and "at least one" can be used interchangeably herein. It is also to be noted that the terms "comprising," "including," and "having" can be used interchangeably.

The term "automatic" and variations thereof, as used herein, refers to any process or operation, which is typically continuous or semi-continuous, done without material human input when the process or operation is performed. However, a process or operation can be automatic, even though performance of the process or operation uses material or immaterial human input, if the input is received before performance of the process or operation. Human input is deemed to be material if such input influences how the process or operation will be performed. Human input that consents to the performance of the process or operation is not deemed to be "material."

Aspects of the present disclosure may take the form of an implementation that is entirely hardware, an implementation that is entirely software (including firmware, resident software, micro-code, etc.) or an implementation combining software and hardware aspects that may all generally be referred to herein as a "circuit," "module," or "system." Any combination of one or more computer-readable medium(s) may be utilized. The computer-readable medium may be a computer-readable signal medium or a computer-readable storage medium.

A computer-readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer-readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer-readable storage medium may be any tangible medium that can contain or store a program for use by or in connection with an instruction execution system, apparatus, or device.

A computer-readable signal medium may include a propagated data signal with computer-readable program code embodied therein, for example, in baseband or as part of a carrier wave. Such a propagated signal may take any of a variety of forms, including, but not limited to, electromagnetic, optical, or any suitable combination thereof. A computer-readable signal medium may be any computer-readable medium that is not a computer-readable storage medium and that can communicate, propagate, or transport a program for use by or in connection with an instruction execution system, apparatus, or device. Program code embodied on a computer-readable medium may be transmitted using any appropriate medium, including, but not limited to, wireless, wireline, optical fiber cable, RF, etc., or any suitable combination of the foregoing.

The terms "determine," "calculate," "compute," and variations thereof, as used herein, are used interchangeably and include any type of methodology, process, mathematical operation or technique.

What is claimed is:

1. A system comprising:
- a processor; and
- a memory storing instructions thereon that, when executed by the processor, cause the processor to:
  - control a robotic arm, having an infusion device attached thereto, to move to a target object comprising an anatomical element of a patient and insert the infusion device into the target object;
  - control the infusion device attached to the robotic arm to infuse a medical substance into the target object according to a first flow rate;
  - control the robotic arm to withdraw the infusion device from the target object at a withdrawal rate;
  - calculate a remaining capacity included in a volume of the target object based on the withdrawal rate of the infusion device from the target object, the remaining capacity corresponding to a cavity left behind by the infusion device;
  - determine a second flow rate for infusing the medical substance into the target object based on the remaining capacity, the second flow rate being different than the first flow rate; and
  - control the robotic arm to continue withdrawing the infusion device from the target object at the withdrawal rate while controlling the infusion device to infuse, the medical substance into the target object according to the second flow rate.

2. The system of claim 1, wherein the instructions are further executable by the processor to:
- calculate the withdrawal rate based on viscosity of the medical substance.

3. The system of claim 2, wherein the withdrawal rate raises as the viscosity lowers.

4. The system of claim 1, wherein the instructions are further executable by the processor to:
- calculate the withdrawal rate based at least in part on one or more properties associated with the medical substance.

5. The system of claim 1, wherein the instructions are further executable by the processor to:
- compare an elapsed duration associated with infusing the medical substance to a temporal threshold; and
- adjust the withdrawal rate based at least in part on a result of the comparison.

6. The system of claim 1, wherein the instructions are further executable by the processor to:
- determine an insertion depth of the infusion device with respect to the target object, based at least in part on image data including the target object; and
- setting the first flow rate based at least in part on:
  - determining the insertion depth; and
  - one or more dimensions of the infusion device.

7. The system of claim 1, wherein the instructions are further executable by the processor to:
- determine a target approach angle of the infusion device with respect to the target object, based at least in part on image data including the target object; and
- set the first flow rate based at least in part on the target approach angle.

8. The system of claim 1, wherein the instructions are further executable by the processor to:
- provide to a machine learning model, at least one of:
  - image data including the target object and the infusion device;
  - one or more properties associated with the medical substance; and
  - one or more properties associated with the infusion device; and
- receive an output from the machine learning model in response to the machine learning model processing at least one of the image data, the one or more properties associated with the medical substance, and the one or more properties associated with the infusion device, wherein the output comprises one or more parameters associated with infusing the medical substance into the target object.

9. The system of claim 8, wherein the one or more parameters comprise:
- the withdrawal rate;
- the first flow rate; and
- the second flow rate.

10. A system comprising:

an infusion device;

a robot including a robotic arm;

a processor; and a memory storing instructions thereon that, when processed by the processor, cause the processor to:

control the robotic arm, having the infusion device attached thereto, to move to a target object comprising an anatomical element of a patient and to insert the infusion device into the target object;

control the infusion device attached to the robotic arm to infuse a medical substance into the target object according to a first flow rate;

control the robotic arm to withdraw the infusion device from the target object at a withdrawal rate;

calculate a remaining capacity included in a volume of the target object based on the withdrawal rate of the infusion device from the target object, the remaining capacity corresponding to a cavity left behind by the infusion device;

determine a second flow rate for infusing the medical substance into the target object based on the remaining capacity, the second flow rate being different than the first flow rate; and control the robotic arm to continue withdrawing the infusion device from the target object at the withdrawal rate while controlling the infusion device to infuse the medical substance into the target object according to the second flow rate.

11. The system of claim 10, wherein the instructions are further executable by the processor to:

calculate the withdrawal rate based on viscosity of the medical substance.

12. The system of claim 10, wherein the instructions are further executable by the processor to:

calculate the remaining capacity further based on one or more dimensions of the infusion device.

13. The system of claim 10, wherein the instructions are further executable by the processor to:

calculate the withdrawal rate based at least in part on one or more properties associated with the medical substance.

14. The system of claim 10, wherein the instructions are further executable by the processor to:

compare an elapsed duration associated with infusing the medical substance to a temporal threshold; and adjust the withdrawal rate based at least in part on a result of the comparison.

15. The system of claim 10, wherein the instructions are further executable by the processor to:

determine an insertion depth of the infusion device with respect to the target object, based at least in part on image data including the target object; and setting the first flow rate based at least in part on:

determining the insertion depth; and one or more dimensions of the infusion device.

16. The system of claim 10, wherein the instructions are further executable by the processor to:

determine a target approach angle of the infusion device with respect to the target object, based at least in part on image data including the target object; and set the first flow rate based at least in part on the target approach angle.

17. The system of claim 10, wherein the instructions are further executable by the processor to:

provide to a machine learning model, at least one of:

image data including the target object and the infusion device;

one or more properties associated with the medical substance; and one or more properties associated with the infusion device; and receive an output from the machine learning model in response to the machine learning model processing at least one of the image data, the one or more properties associated with the medical substance, and the one or more properties associated with the infusion device, wherein the output comprises one or more parameters associated with infusing the medical substance into the target object.

18. A method comprising:

controlling a robotic arm, having an infusion device attached thereto, to move to a target object comprising an anatomical element of a patient and to insert the infusion device into the target object;

controlling the infusion device attached to the robotic arm to infuse a medical substance into the target object according to a first flow rate;

controlling the robotic arm to withdraw the infusion device from the target object at a withdrawal rate;

calculating a remaining capacity included in a volume of the target object based on the withdrawal rate of the infusion device from the target object, the remaining capacity corresponding to a cavity left behind by the infusion device;

determining a second flow rate for infusing the medical substance into the target object based on the remaining capacity, the second flow rate being different than the first flow rate; and controlling the robotic arm to continue withdrawing the infusion device from the target object at the withdrawal rate while controlling the infusion device to infuse the medical substance into the target object according to the second flow rate.

19. The method of claim 18, wherein the withdrawal rate is calculated based on viscosity of the medical substance.

20. The method of claim 18, wherein the remaining capacity is calculated further based on one or more dimensions of the infusion device.

21. The method of claim 18, further comprising:

calculating the withdrawal rate based at least in part on one or more properties associated with the medical substance.

22. The method of claim 18, further comprising:

comparing an elapsed duration associated with infusing the medical substance to a temporal threshold; and adjusting the withdrawal rate based at least in part on a result of the comparison.

23. The method of claim 18, further comprising:

determining an insertion depth of the infusion device with respect to the target object, based at least in part on image data including the target object; and setting the first flow rate based at least in part on:

determining the insertion depth; and one or more dimensions of the infusion device.

24. The method of claim 18, further comprising:

determining a target approach angle of the infusion device with respect to the target object, based at least in part on image data including the target object; and setting the first flow rate based at least in part on the target approach angle.

25. The method of claim 18, further comprising:

providing to a machine learning model, at least one of:
image data including the target object and the infusion device;
one or more properties associated with the medical substance; and
one or more properties associated with the infusion device; and receiving an output from the machine learning model in response to the machine learning model processing at least one of the image data, the one or more properties associated with the medical substance, and the one or more properties associated with the infusion device, wherein the output comprises one or more parameters associated with infusing the medical substance into the target object.

26. A system, comprising:

an infusion device;

a robotic arm attach to the infusion device;

a computing device comprising a processor, communication interface, and memory;

the memory storing instructions thereon that, when processed by the processor, cause the processor to:
controlling the robotic arm to move to a target object comprising an anatomical element of a patient and to insert the infusion device into the target object;
controlling the infusion device attached to the robotic arm to infuse a medical substance into the target object according to a first flow rate;
controlling the robotic arm to withdraw the infusion device from the target object at a withdrawal rate;
calculating a remaining capacity included in a volume of the target object based on the withdrawal rate of the infusion device from the target object, the remaining capacity corresponding to a cavity left behind by the infusion device;
determining a second flow rate for infusing the medical substance into the target object based on the remaining capacity, the second flow rate being different than the first flow rate; and
controlling the robotic arm to continue withdrawing the infusion device from the target object at the withdrawal rate while controlling the infusion device to infuse the medical substance into the target object according to the second flow rate.

27. The system of claim 26, wherein the instructions are further executable by the processor to:
calculate the withdrawal rate based on viscosity of the medical substance.

28. The system of claim 26, wherein the instructions are further executable by the processor to:
calculate the remaining capacity further based on one or more dimensions of the infusion device.

29. The system of claim 26, wherein the instructions are further executable by the processor to:
calculate the withdrawal rate based at least in part on one or more properties associated with the medical substance.

30. A non-transitory computer readable medium comprising instructions, which when executed by a processor:
control a robotic arm, having an infusion device attached thereto, to move to a target object comprising an anatomical element of a patient and to insert the infusion device into the target object;
control the infusion device attached to the robotic arm to infuse a medical substance into the target object according to a first flow rate;
control the robotic arm to withdraw the infusion device from the target object at a withdrawal rate;
calculate a remaining capacity included in a volume of the target object based on the withdrawal rate of the infusion device from the target object, the remaining capacity corresponding to a cavity left behind by the infusion device;
determine a second flow rate for infusing the medical substance into the target object based on the remaining capacity, the second flow rate being different than the first flow rate; and
control the robotic arm to continue withdrawing the infusion device from the target object at the withdrawal rate while controlling the infusion device to infuse the medical substance into the target object according to the second flow rate.

* * * * *